(12) United States Patent
Moussy et al.

(10) Patent No.: US 6,366,794 B1
(45) Date of Patent: Apr. 2, 2002

(54) GENERIC INTEGRATED IMPLANTABLE POTENTIOSTAT TELEMETRY UNIT FOR ELECTROCHEMICAL SENSORS

(75) Inventors: Francis Moussy, Farmington, CT (US); Robert W. Conlan, Niceville; Markham C. Godwin, Navarre, both of FL (US); Richard D. Beach, Windsor, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 09/443,764

(22) Filed: Nov. 19, 1999

Related U.S. Application Data
(60) Provisional application No. 60/109,289, filed on Nov. 20, 1998.

(51) Int. Cl.[7] ................................................. A61G 5/05
(52) U.S. Cl. ........................................ 600/345; 600/365
(58) Field of Search ................................. 600/345–350, 600/365

(56) References Cited

U.S. PATENT DOCUMENTS

| | | | |
|---|---|---|---|
| 4,633,878 A | | 1/1987 | Bombardieri |
| 4,703,756 A | | 11/1987 | Gough et al. |
| 5,368,028 A | * | 11/1994 | Palti ............................ 600/345 |
| 5,411,551 A | * | 5/1995 | Winston et al. ............. 600/347 |
| 5,914,026 A | | 6/1999 | Blubaugh, Jr. et al. |
| 6,175,752 B1 | * | 1/2001 | Say et al. .................... 600/365 |
| 6,210,326 B1 | * | 4/2001 | Ehwald ........................ 600/347 |
| 6,212,416 B1 | * | 4/2001 | Ward et al. .................. 600/347 |

FOREIGN PATENT DOCUMENTS

| | | |
|---|---|---|
| EP | 0 554 955 A1 | 4/1993 |
| WO | WO 91/01680 | 2/1991 |
| WO | WO 97/19344 | 5/1997 |

OTHER PUBLICATIONS

Shults, Mark C., et al, "A Telemetry–Instrumentation System for Monitoring Multiple Subcutaneously Implanted Glucose Sensors" IEEE Transactions on Biomedical Engineering, Oct. 1994, vol. 41, p. 10, pp. 937–942.

Atanasov, et al, "In vivo rechargeable glucose biosensors" Sensors and Actuators B, CH, Elsevier Sequoia S. A., Lausanne, vol. B36, No. 01/02/03, Oct. 1996, pp. 435–447.

M.J. Conway, Msc; D. Parker, PhD; and L.P. Soutter, Phd, "Radio Telemetry of blood p02 in vivo", Biomedical Engineering, vol. 8, No. 10. Oct., 1973.

Joseph Black, Michael Wilkins, Plamen Atanasov & Ebtisam Wilkins "Integrated sensor–telemetry system for in vivo glucose monitoring" Sensors and Actuators B Chemical, vol. B31, No. 3, completing vol. B31, Mar. 1996–Elsevier Science S.A.

Mark C. Shults, Rathbun K. Rhodes, Stuart J. Updike, Barbara J. Gilligan and William N. Reining "A Telemetry–Instrumentation System for Monitoring Multiple Subcutaneously Implanted Glucose Sensors" IEEE Transactions on Biomedical Engineering, vol. 41, No. 10, Oct. 1994;.

Wen H. Ko, "Implantable Sensors For Closed–Loop Prosthetic Systems", Futura Publishing Company, Inc., Mount Kisco, NY; 1985.

Brian D. McKean and David A. Gough, A Telemetry–Instrumentation System for Chronically Implanted Glucose and Oxygen Sensors, IEEE Transaction on Biomedical Engineering, vol. 35, No. 7, Jul. 1988.

W. Sansen, J. Celen, F. Colin and O. Garcia "Implantable Glucose Measurement System", Frontiers of Engineering and Computing in Health Care–1983—Proceedings–Fifth Annual Conference in Medicine and Biology Society.

* cited by examiner

*Primary Examiner*—Robert S. Nasser
(74) *Attorney, Agent, or Firm*—Cantor Colburn LLP

(57) ABSTRACT

A generic implantable puck that can be used with a number of biosensor configurations. This generic implantable potentiostat telemetry unit (the puck) can also be part of a system to detect glucose concentrations. An electrochemical system partially implantable into a body for detecting glucose concentrations therein is presented. The system comprises an electrochemical sensor, a transmitting puck including an electric circuit connected to the electrochemical sensor for transmitting a signal indicative of the glucose concentrations in the body. There is at least one receiver for receiving the signal from the transmitting puck and a computer system coupled tlo the at least one receiver for processing the signal for patient diagnosis and treatment.

52 Claims, 4 Drawing Sheets

GENERIC INTEGRATED IMPLANTABLE POTENTIOSTAT TELEMETRY UNIT FOR ELECTROCHEMICAL SENSORS

RELATED APPLICATIONS

This application claims the benefit of provisional application No. 60/109,289 filed on Nov. 20, 1998 which is hereby incorporated by reference in its entirety.

TECHNICAL FIELD

This invention relates to an electrochemical system partly implantable into a body for detecting glucose concentrations therein and in a similar fashion, other elements, compounds or analytes.

BACKGROUND OF THE INVENTION

There is a need for an implantable generic device that can be used with different types of electrochemical sensors to facilitate real time monitoring during sensor development. Such a device would be an integrated potentiostat telemetry transmitting unit allowing researchers to test various biosensor configurations for multiple possible uses. In an effort to regulate their glucose levels, diabetic patients monitor their glycemia by repeatedly obtaining a sample of capillary blood by finger-pricking. Since these tests are frequent, painful and time consuming, diabetic patients resist performing an adequate number of these daily glucose measurements. This low compliance, plus the intrinsically discontinuous nature of the technique, leads to the extensive pathology seen in diabetic patients. Thus, a great deal of research is being directed toward the development of new glucose sensors capable of replacing finger-pricking. Such glucose sensors are ideally implantable in the patient, though pain free, as well as small, light-weight and capable of reliable and continuous operation over extended periods of time. In addition it is desirable that such sensors be a part of a system capable of continuous and real time processing of data from the sensors for diagnosis and patient treatment. It is also desirable that the system be easily adaptable to use with various amperometric glucose sensors without the need for redesigning the system for each new sensor. Such a system should be flexible, reliable, stable and easy to use in a telemetried system.

Previous telemetried systems require the development of designs taylored to a specific use and set of requirements. Typical telemetried systems utilize voltage-to-frequency conversion to increase frequency stability during frequency modulation of a carrier signal. This method expends objectionable amounts of power, limiting battery lifetime. The transmitted radio frequency carrier and modulation thereof are continuous battery consuming processes. However, this requires the additional step of demodulation and additional signal shaping circuits in order to recover the data. This requires additional power consumption and increased package size. In addition, data accuracy can be tainted by drift in the transmitter and the receiver components. Typical telemetried systems also required dual battery configurations to provide power, thus adding to size.

It is desirable in a telemetried system to convert glucose sensor data to digital values in vivo, in order to avoid conversion and modulation errors. Once in digital format, a radio transmitter can utilize a serial data transmission protocol to a receiver thence directly to a computer for processing. An on-off-keyed(OOK) asynchronous serial binary character data transmission method expends battery power only for the brief duration of each digital "one" bit. It expends zero power for each digital "zero" bit. In addition to the glucose sensor data, an individual sensor identification code, and error preventive codes are included in each transmission, termed a "packet." These data packets uniquely identify one of any number of sensors and provide a means to verify fidelity of the received data. Stored programs can allow direct conversion to glucose concentrations for immediate readout.

Monitoring glucose concentrations in diabetic patients is seen in U.S. Pat. No. 4,633,878 which relates to feedback controlled or "closed-loop" insulin pumps known also as "artificial pancreases". These devices provide a continuous glucose determination in the diabetic patient. Data is transmitted from a glucose sensor to a microprocessor unit, which controls a pump for insulin, or glucose, infusion in order to maintain blood glucose levels within physiological range. In U.S. Pat. No. 4,703,756 an electrochemical system includes a sensor module suitable for implantation in the body to monitor glucose and oxygen levels therein. In U.S. Pat. No. 5,914,026 an implantable sensor comprising a biocompatable electroconductive case which houses a measuring electrode, a reference electrode, an auxiliary electrode, and an electronic circuit for measuring the response of the measuring electrode where the measuring electrode, reference electrode and auxiliary electrode are not in direct electrical contact with one another is provided.

SUMMARY OF THE INVENTION

This invention describes a generic implantable puck that can be used with a number of biosensor configurations. This generic implantable potentiostat telemetry unit (the puck) can also be part of a system to detect glucose concentrations. An electrochemical system partially implantable into a body for detecting glucose concentrations therein is presented. The system comprises an electrochemical sensor, a transmitting puck including an electric circuit connected to the electrochemical sensor for transmitting a signal indicative of the glucose concentrations in the body. There is at least one receiver for receiving the signal from the transmitting puck and a computer system coupled to the at least one receiver for processing the signal for patient diagnosis and treatment.

EXPLANATION OF THE DRAWINGS

Referring now to the drawings wherein like elements and features are numbered alike in the several figures.

DESCRIPTION OF THE PREFERRED EMBODIMENTS

Figure 1:
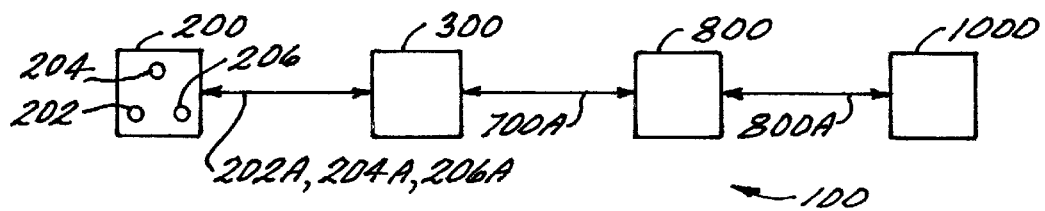
FIG. 1 is a schematic representation of the electrochemical system of the present invention as it is generally comprised of an electrochemical sensor, a transmitting puck, at least one receiver and a computer system.

A description of the preferred embodiment of the present invention will now be had, by way of exemplification and not limitation, with reference to FIGS. 1, 2, 3, 4 and 5 of the drawing. FIG. 1 is a schematic representation of the electrochemical system 100 of the present invention as it is generally comprised of an electrochemical sensor 200, including at least one electrode 202, 204, 206 connected to a transmitting puck 300. The electrochemical sensor 200 and the transmitting puck 300 are implantable into a body. The transmitting puck 300 is operative to generate a sensor current, $I_s$, through the electrochemical sensor 200 which is proportional to the glucose concentrations in the body. The transmitting puck 300 thence transmits a serial digital signal, $V_T$, which is based upon the sensor current, $I_s$, and is indicative of the glucose concentrations. The electrochemical system 100 further includes at least one receiver 800 for receiving the signal, $V_T$. The at least one receiver 800 may comprise a portable receiver 800 worn by a patient implanted with the electrochemical sensor 200 and the transmitting puck 300. Such a portable receiver 800 would contain an onboard microprocessor having the capability of providing a continuous or, if desired, periodic readout of the patients glucose concentration, as well as the ability to retain such information in memory and to warn the patient when glucose concentrations are too high or too low. The at least one receiver 800 may also comprise a larger office version connected to a computer system 1000 for processing the serial digital signal, $V_T$, for patient diagnosis and treatment.

Figure 2:
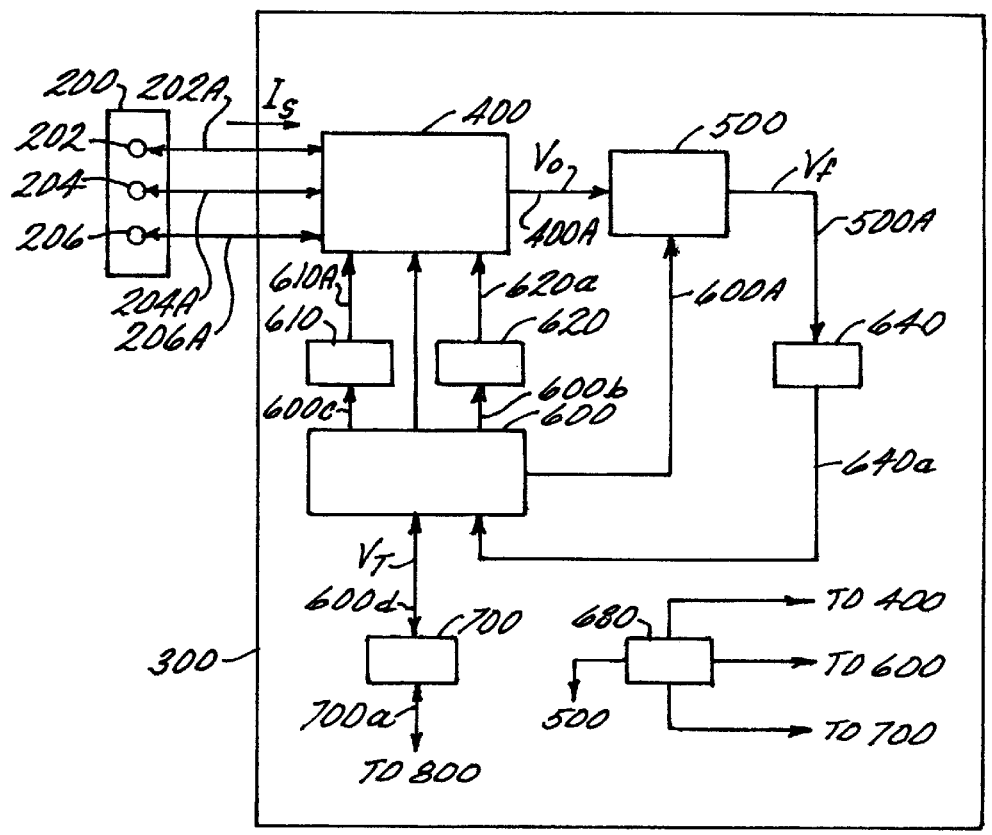
FIG. 2 is a schematic representation of the electric circuit of the transmitting puck.

Reference will now be had to FIG. 2. Therein depicted is a schematic representation of the transmitting puck 300 including an electric circuit connected to the electrochemical sensor 200. The electrochemical sensor 200 includes at least one electrode, 202, 204, 206. The first electrode 202 of the at least one electrode is commonly referred to as the auxiliary electrode and provides a driving voltage to the electrochemical sensor 200. The second electrode 204 is commonly referred to as the reference electrode and allows for compensation of circuit and solution losses. The third electrode 206 is commonly referred to as the working electrode wherein the electrochemical reaction occurs.

The electric circuit of the transmitting puck 300 includes a power supply 680 for energizing the elements of the electric circuit. A potentiostat circuit 400 is connected to at the least one electrode 202, 204, 206 of the electrochemical sensor 200. The potentiostat circuit 400 is further connected to a first digital-to-analog converter 610, a second digital-to-analog converter 620, to a microprocessor 600 and to at least one filter circuit 500. The first digital-to-analog converter 610 provides an excitation voltage, $V_i$, to the electrochemical sensor 200. The nature of the excitation voltage, $V_i$, is controlled by the microprocessor 600 through the first digital to analog converter 610 and may, for example, be a constant voltage or a ramped voltage or a sinusoidal voltage or a sawtooth voltage signal. Such cyclic voltammetry allows for the characterization and testing of the electrochemical sensor 200. The second digital-to-analog converter 620 provides an adjustable reference voltage, $V_g$, to the potentiostat circuit 400 in order to allow for bipolar functioning of the electrochemical sensor 200. The microprocessor 600 is directly connected to the potentiostat circuit 400 to provide gain adjustment of the potentiostat circuit 400 and also to the at least one filter circuit 500 to provide adjustments of filter characteristics.

Continuing in FIG. 2, the potentiostat circuit 400 is operative to generate the sensor current, $I_s$, through the electrochemical sensor 200 and to thence convert $I_s$ into an output voltage, $V_o$, proportional to glucose concentrations. The output voltage, $V_o$, is then passed through the at least one filter circuit 500 for filtering of unwanted signals. A filtered signal, $V_f$, is then converted into digital form by an analog-to-digital converter 640 and thence conveyed to the microprocessor 600, whereupon a serial data signal, $V_T$, is conveyed to the transmitter 700.

Figure 3:
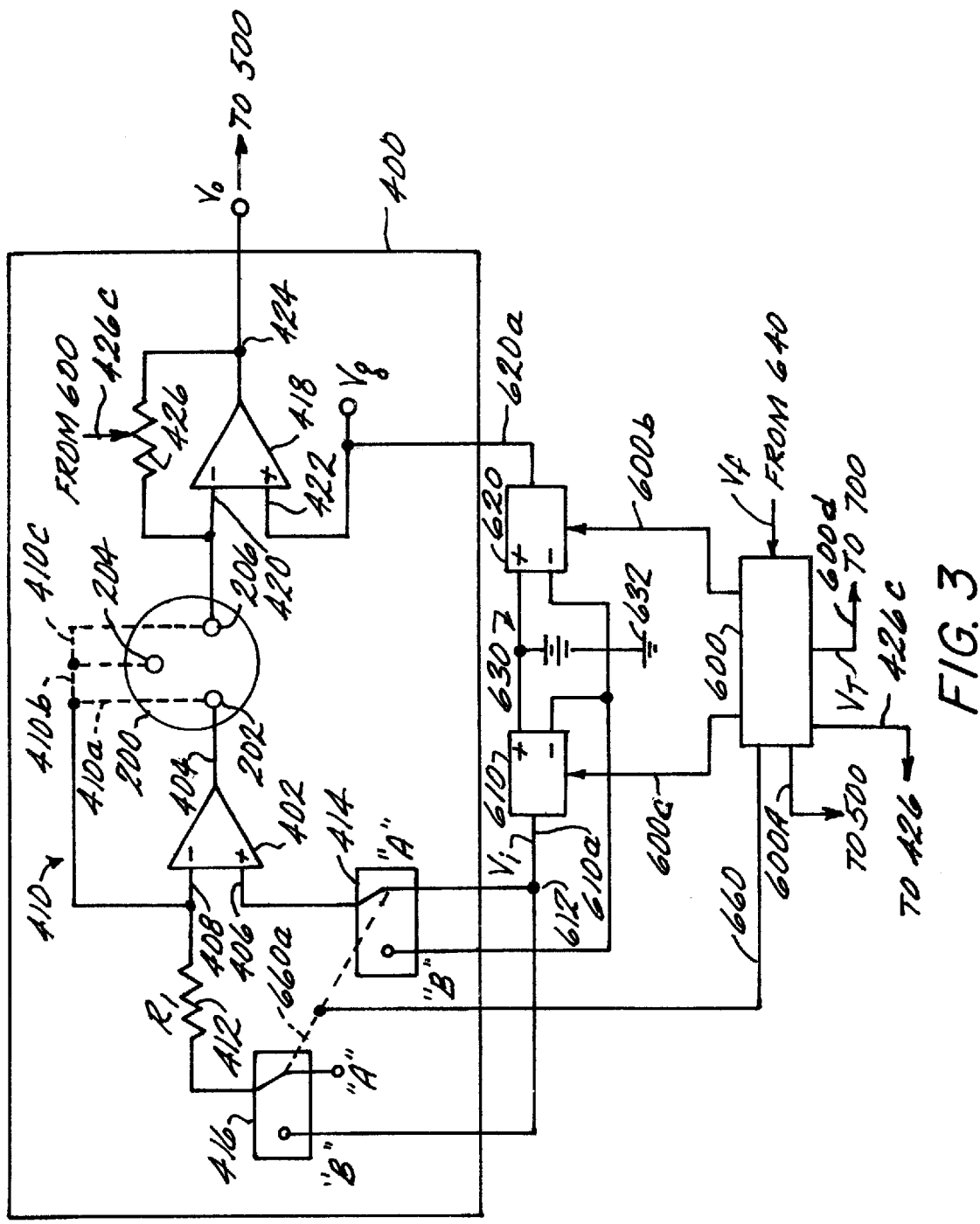
FIG. 3 is a first schematic representation of the potentiostat circuit of the transmitting puck.

Reference will now be had to FIG. 3. Therein depicted is a schematic representation of the potentiostat circuit 400 of the transmitting puck 300. The potentiostat circuit 400 comprises a first operational amplifier 402 having a first output terminal 404 connected to a first electrode 202 of the at least one electrode 202, 204, 206. The first operational amplifier 402 also includes a first input terminal 406 connected to a single pole-double throw first switch 414, and a second input terminal 408. The first operational amplifier 402 includes a first feedback circuit 410 connected firstly to a selected one electrode of the at least one electrode 202, 204, 206 and secondly to the second input terminal 408 and a single pole-single throw second switch 416. The first and second switches 414, 416 are thrown simultaneously and controlled by the microprocessor 600 by way of signal path 660. The first feedback circuit 410 comprises a direct connection between the selected one electrode and the second input terminal 408 and a first resistor 412, $R_1$, between the second input terminal 408 and the second switch 416. The direct connection between the second input terminal 408 and the selected one electrode may be of one of three configurations as designated by the reference numerals 410a, 410b and 410c. In a first configuration 410a, the first feedback circuit 410 is connected to the auxiliary electrode 202, thus providing a driving voltage at the auxiliary electrode 202. In a second configuration 410b, the first feedback circuit 410 is connected to the reference electrode 204, thus providing compensation for circuit and solution losses. In a third configuration 410c, the first feedback circuit 410 is connected to the working electrode 206. The potentiostat circuit 400 further comprises a second operational amplifier 418 having a third input terminal 420 connected to a third electrode 206 of the at least one electrode 202, 204, 206, a fourth input terminal 422 connected to the second digital-to-analog converter 620 of the first at least one signal converter, a second output terminal 424 and a second feedback circuit 426 connected to the second output terminal 424, the third input terminal 420 and the microprocessor 600. The second feedback circuit 426 comprises a second resistor, $R_2$, which may be a digital resistor controlled by the microprocessor 600.

Continuing in FIG. 3, the potentiostat circuit 400 is connected to the first digital-to-analog converter 610 and a second digital-to-analog converter 620 which are biased by a first reference voltage, $V_r$, 630. The first digital-to-analog converter 610 is connected to the microprocessor 600 and operative thereby to accept as input therefrom a digital signal. The first digital-to-analog converter 610 thereby provides as output an analog excitation voltage, $V_i$, at node 612 which may be, for example, a constant voltage or a ramped voltage or a sawtooth voltage or a sinusoidal voltage. The second digital-to-analog converter 620 is connected to the microprocessor 600 and operative thereby to accept as input therefrom a digital signal. The second digital-to-analog converter 620 thereby provides as output a second reference voltage, $V_g$, at the fourth input terminal 422 thus allowing for the bipolar functioning of the electrochemical sensor 200.

The function of the potentiostat circuit 400 may be accomplished in one of several modes, i.e., by the aforementioned selection of the configuration of the first feedback circuit 410 coupled with the simultaneous switching of the first switch 414 and the second switch 416 to a first position, "A" (as shown in FIG. 3), or a second position, "B." As an example, if the first switch 414 and the second switch 416 are in position "A" and the first feedback circuit 410 is connected to the auxiliary electrode 202, then the potentiostat circuit 400 functions as a two-wire potentiostat. If the first switch 414 and the second switch 416 are in position "A" and the first feedback circuit 410 is connected to the reference electrode 204, then the potentiostat circuit 400 functions as a three-wire potentiostat. If the first switch 414 and the second switch 416 are in position "B" and the first feedback circuit 410 is connected to the working electrode 206, then the potentiostat circuit 400 functions as a two-wire galvanostat. It will be appreciated that when functioning as such a two-wire galvanostat the third input terminal 420 is disconnected from the working electrode 206.

Figure 4:
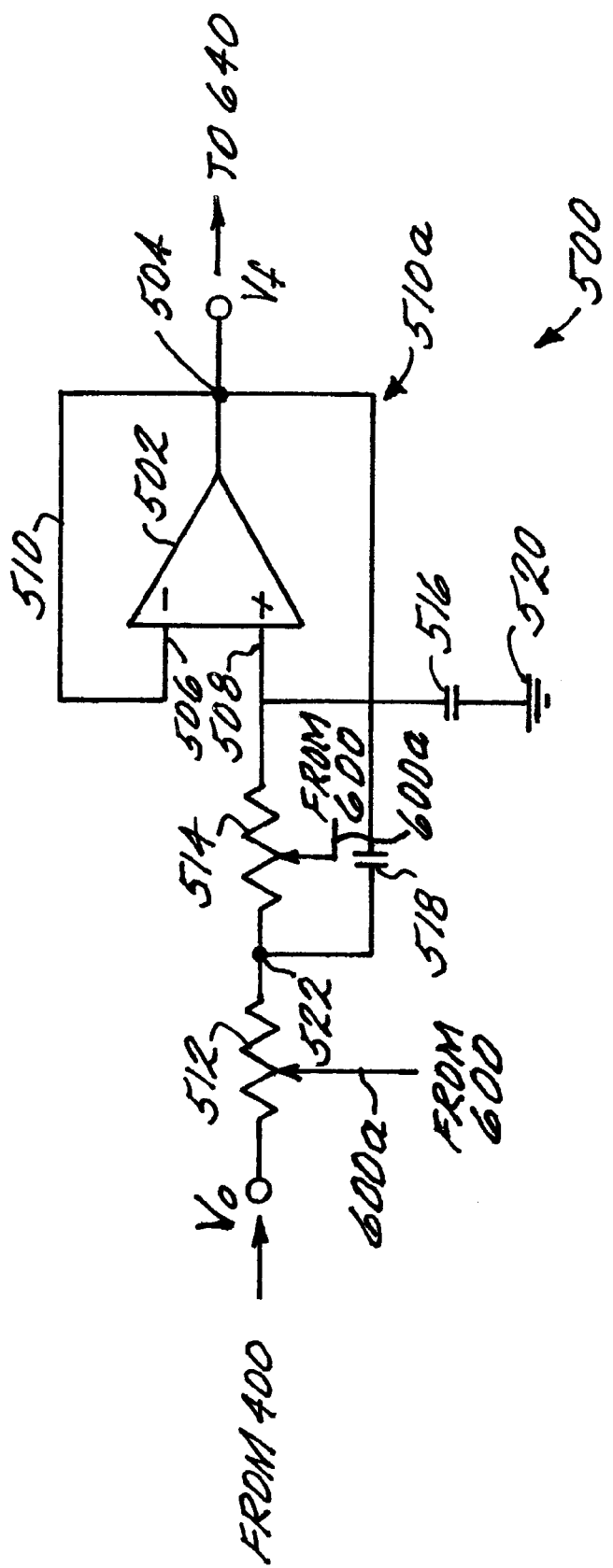
FIG. 4 is a schematic representation of the electric filter circuit of the electric circuit of the transmitting puck.

Reference will now be had to FIG. 4. Therein depicted is a generalized schematic representation of the filter circuit 500. The filter circuit 500 is comprised of a third operational amplifier 502 having a third output terminal 504, a fifth input terminal 506 and a sixth input terminal 508. The third operational amplifier 502 further includes a third feedback circuit 510 connected to the third output terminal 504 and the fifth input terminal 506. The third operational amplifier 502 includes a fourth feedback circuit 510a. Therein, the sixth input terminal 508 is connected to a third reference voltage 520 by way of a first capacitor 516. A third resistor 512 and a fourth resistor 514 are connected to the sixth input terminal 508. The third output terminal 504 is connected to a node point 522 between the third resistor 512 and fourth resistor 514 by way of a second capacitor 518. Such a filter circuit 500 is a second order filter and its filtering capabilities are established by a judicious selection of the values of the third resistor 512, fourth resistor 514, first capacitor 516 and second capacitor 518. In addition the operative nature of the filter circuit 500 may be enhanced by placing the filter circuit 500 either in series or parallel with the same or like filters. Such filters may also be controlled by the microprocessor 600. The filter circuit 500 is thus operative to accept as input thereto, the output voltage, $V_o$, of the potentiostat circuit 400 and provide as output therefrom an appropriately filtered signal, $V_f$. The filtered signal, $V_f$, is indicative of the glucose concentrations and is conveyed to a first analog-to-digital converter 640 where it is converted into a digital form and thence conveyed to the microprocessor 600 whereupon a serial digital signal, $V_T$, is conveyed to the transmitter 700. The transmitter 700 then in turn conveys $V_T$ to the aforesaid at least one receiver 800.

Figure 5:
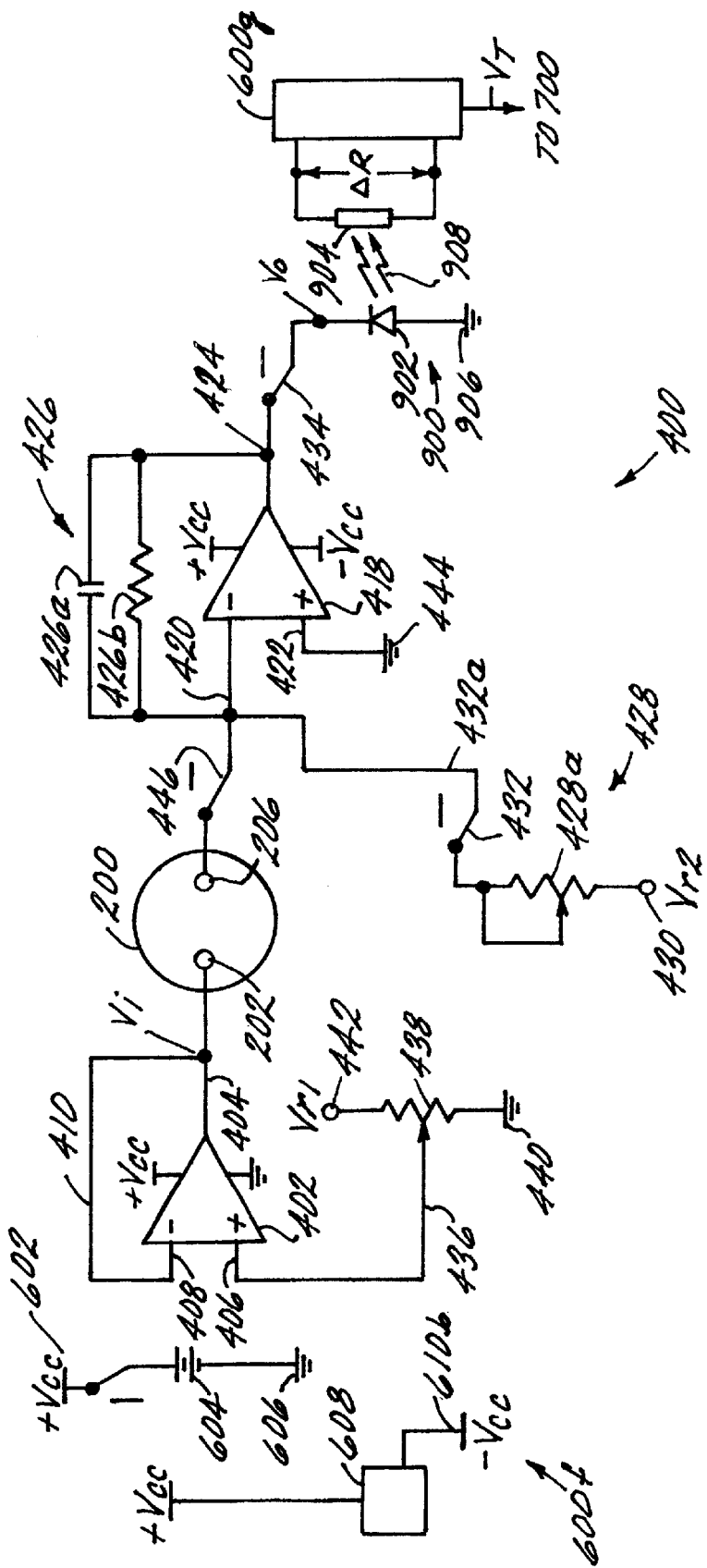
FIG. 5 is a second schematic representation of the potentiostat circuit of the transmitting puck.

Reference will now be had to FIG. 5. Therein depicted is a schematic representation of an alternate to the potentiostat circuit 400 of FIG. 3 connected to a two electrode electrochemical sensor 200. The positive terminal of a battery 604 is connected to a third switch 602 and the negative terminal thereof is connected to electrical ground 606. The power supply 600f is thereby operative to energize the first operational amplifier 402 and the second operational amplifier 418 with the supply voltage, $+V_{cc}$, when the thirdswitch 602 is in the closed position (as shown). A voltage converter 608 supplies $-V_{cc}$ to the second operational amplifier 418. It is contemplated that $+/-V_{cc}$ is approximately $+/-3.7$ volts. When the thirdswitch 602 is in the open position, the first operational amplifier 402 and second operational amplifier 418, are deenergized. The first input terminal 408 of the first operational amplifier 402 is an inverting terminal and the second input terminal 406 is a non-inverting terminal. The first feedback circuit 410 is a direct connection between the first output terminal 404 and the first input terminal 408. A potentiometer 438 comprises a voltage divider 436 connected to a fourth reference voltage 442, held at a potential of $+V_{r1}$ volts, and a fifth reference voltage 440, held at electrical ground. The voltage divider 436 is also connected to the non-inverting terminal 406. Thus, the first operational amplifier 402 is operative to maintain the first output terminal 404, and thus the first electrode 202 of the electrochemical sensor 200, at the substantially constant excitation voltage, $V_i$. In particular, by adjusting the voltage divider 436, the excitation voltage, $V_i$, may be varied from 0 volts to $V_{r1}$ volts. Thus, the first operational amplifier 402 acts, for example, in a fashion that is commonly referred to as a voltage follower. It is contemplated that $V_{r1}$ is approximately +1.2 volts and the potentiometer 436 is adjusted so as to make excitation voltage, $V_i$, approximately +0.7 volts to provide glucose concentration related data.

Continuing in FIG. 5, the third input terminal 420 of the second operational amplifier 418 is an inverting terminal and the fourth input terminal 422 is a non-inverting terminal connected to electrical ground 444. A third switch 446 is a two position switch that connects the second electrode 206 of the electrochemical sensor 200 to the third input terminal 420 and turns the electrochemical sensor 200 On or Off. The voltage at the second electrode 206, $V_w$, varies with the glucose concentration thus resulting in a voltage drop, $\Delta V = V_i - V_w$, across the first electrode 202 and the second electrode 206. The voltage drop, $\Delta V$ coupled with the impedance of the glucose, $Z_g$, generate the aforesaid sensor current, $I_s$. The second feedback circuit 426 comprises a capacitor 426a in parallel with a resistor 426b. The resistor 426b acts to set the amplifier gain and in conjunction with the capacitor 426a, acts as a low pass filter in order to dampen high frequency noise. An offset current compensation circuit 428 comprises a variable resistor 428a connected to a fourth switch 432 and the sixth reference voltage 430 held at a potential of Vr2 volts. The fourth switch 432 is a two position switch that engages or disengages the offset current compensation circuit 428. With the fourth switch 432 in the closed position (as shown) and by adjusting the variable resistor 428a, an offset bias current, $I_B$, is established at third input terminal 420. Continuing in FIG. 5, a fifth switch 434 is a two position switch that turns an optocoupler 900 On or Off. The second operational amplifier 418 is thereby operative to convert the sensor current, $I_s + I_B$, into an output voltage, $V_o$, at the second output terminal 424 and thus acts, for example, in a fashion that is referred to as a transimpedence amplifier.

Continuing in FIG. 5, the second operational amplifier 418 is connected to the optocoupler 900 by way of the fifth switch 434. The optocoupler 900 comprises a first optical device 902, such as a light emitting diode. The first optical device 902 is optically coupled to a second optical device 904 such as a photocell, a photosensitive resistor or a phototransistor. The cathode of the first optical device 902 is connected to the fifth switch 434 and the anode is connected to electrical ground 906. As such, when the output voltage, $V_o$, at the second output terminal 424 or the fifth switch 434 is negative, the first optical device 902 emits an optical signal 908 to which the second optical device 904 is responsive. The operative nature of the first optical device 902 is such that the optical signal 908 emitted therefrom is consistent with the output voltage, $V_o$, at the second output terminal 424 when the third switch 434 is closed (as shown). The optocoupler 900 is connected to the microprocessor 600 via the second optical device 904. However, the nature of the coupling of the first optical device 902 and the second optical device 904 via the optical signal 908 is such as to provide electrical isolation of the microprocessor 600 from the potentiostat circuit 400. As a result of the aforesaid responsivity of the second optical device 904 to the optical signal 908, a changing resistance, ΔR, is developed across the second optical device 904. The output, ΔR, of the second optical device 904 is conveyed to the microprocessor 600 for conversion to a digital serial data signal, $V_T$, which is then conveyed to the transmitter 700. The transmitter 700 is operative to transmit a digital serial data signal $V_T$, indicative of the changing resistance, ΔR, in the optocoupler 900 to the at least one receiver 800. $V_T$ is then conveyed to the computer system 1000 for processing thereof by appropriate controlling software, e.g., screen readout and data logging to a storage disk. It is contemplated that the aforesaid transmittal of the serial data signal, $V_T$, is by a radio frequency electromagnetic wave at a carrier frequency of about 303.85 Mhz. In particular, $V_T$ is in the nature of digital counts whereby 1 digital count=10 ΔR ohms. The serial data signal, $V_T$, includes, for example, the transmitter serial number, the resistance value in the number of digital counts and a timing scheme governing data transmission rates, data logging rates and received data error prevention information. $V_T$ is conveyed from the at least one receiver 800 to the computer system 1000 whereat actual glucose concentration values are displayed on a computer screen for immediate readout provided by real time conversion of digital counts based upon earlier calibration, curve fitting and tables. The computer system 1000 is operative to initialize the status of the transmitting puck 300, deactivate the transmitting puck 300, error check $V_T$, process $V_T$ for display to a screen, log $V_T$ to a disk file and commands the transmitting puck 300 to set transmission intervals over a range from 5 seconds to 10 minutes.

Thus it will be appreciated that the electrochemical system provides real time continuous and reliable data related to the glucose concentrations in a body. The microprocessor 600 controls the status of the potentiostat circuit 400 by controlling the first and second switches 414, 416, controls the bias voltage, $V_g$, the excitation voltage, $V_i$, establishes alarm levels and directs the transmission of $V_T$. The transmitter 700, including a near field receiver, accepts as input from the microprocessor 600 the serial data value, $V_T$, in a serial data protocol and by digital signal processing converts $V_T$ into a binary stream to be conveyed to the at least one receiver 800. The at least one receiver 800 accepts as input the binary stream and recovers therefrom the serial data signal, $V_T$, for conveyance to either the computer system 1000 for processing thereof or immediate display to a patient. The at least one receiver 800 includes a near field transmitter operative to initialize the transmitting puck 300 and place the transmitting puck 300 in standby mode.

While preferred embodiments have been shown and described, various modifications and substitutions may be made thereto without departing from the true spirit and scope of the invention. Accordingly, it is understood that the present invention has been described by way of illustrations and not limitation.

What is claimed is:

1. An electrochemical system for detecting glucose concentrations in a body, the system comprising:
   an electrochemical sensor for implantation into the body including at least one electrode;
   a telemetry unit for implantation into the body including an electric circuit having a first operational amplifier having a first output terminal connected to a first electrode of the at least one electrode, means for switching the electric circuit between a potentiostat circuit and a galvanostat circuit providing thereby an excitation voltage to a first electrode of the at least one electrode of the electrochemical sensor and generating thereby a first signal indicative of glucose concentrations;
   wherein the first operational amplifier includes first and second input terminals connected to means for switching the electric circuit between a potentiostat circuit and a galvanostat circuit and a first feedback circuit having at least one electric device therein connected to a second electrode of the at least one electrode, the second input terminal and means for switching means the electric circuit between a potentiostat circuit and a galvanostat circuit;
   at least one signal converter connected to means for switching the electric circuit between a potentiostat circuit and a galvanostat circuit;
   a microprocessor connected to means for switching the electric circuit between a potentiostat circuit and a galvanostat circuit and to the at least one signal converter for controlling switching the electric circuit between a potentiostat circuit and a galvanostat circuit;
   at least one receiver for receiving the signal from the telemetry unit; and
   a power supply for energizing the electric circuit.

2. The electrochemical system as set forth in claim 1 further comprising:
   a second operational amplifier having
   a third input terminal connected to a third electrode of the at least one electrode,
   a fourth input terminal connected to the at least one signal converter, a second output terminal; and
   a second feedback circuit having at least one electric device therein connected to the second output terminal, the third input terminal and the microprocessor.

3. The electrochemical system as set forth in claim 2 wherein the first feedback circuit is a negative feedback circuit including a direct connection from the first output terminal to the second input terminal.

4. The electrochemical system as set forth in claim 2 wherein the first feedback circuit is a negative feedback circuit including a first resistor connected to the second input terminal and the second switch.

5. The electrochemical system as set forth in claim 2 wherein the second feedback circuit is a negative feedback circuit including a second resistor connected to the second output terminal and the third input terminal.

6. The electrochemical system as set forth in claim 5 wherein the second resistor is controlled by the microprocessor.

7. The electrochemical system as set forth in claim 2 wherein the second electrode of the at least one electrode is an auxiliary electrode.

8. The electrochemical system as set forth in claim 2 wherein the second electrode of the at least one electrode is a reference electrode.

9. The electrochemical system as set forth in claim 2 wherein the second electrode of the at least one electrode is a working electrode and the third input terminal is disconnected from the third electrode.

10. The electrochemical system as set forth in claim 1 wherein the electric circuit further comprises a filter circuit connected to the potentiostat circuit and the at least one signal converter.

11. The electrochemical system as set forth in claim 10 wherein the filter circuit is a low pass filter circuit.

12. The electrochemical system as set forth in claim 11 wherein the filter circuit comprises:
   a first operational amplifier having
   a first output terminal connected to the at least one signal converter;

a first input terminal;
a second input terminal
a first feedback circuit having at least one electrical device therein connected to the first output terminal and the first input terminal;
a second feedback circuit having at least one electrical device therein connected to the first output terminal and the second input terminal.

13. The electrochemical system as set forth in claim 12 wherein the first feedback circuit is a negative feedback circuit.

14. The electrochemical system as set forth in claim 12 wherein the first feedback circuit comprises a direct connection.

15. The electrochemical system as set forth in claim 12 wherein the second feedback circuit is a positive feedback circuit.

16. The electrochemical system as set forth in claim 12 wherein the second feedback circuit comprises:
a first capacitor connected to the second input terminal and a first reference voltage;
a first resistor connected to the second input terminal,
a second capacitor connected to the first output terminal and the first resistor; and
a second resistor connected to the first resistor and the second capacitor.

17. The electrochemical system as set forth in claim 1 wherein the electric circuit further comprises a transmitter connected to the microprocessor for transmitting a signal indicative of glucose concentrations.

18. The electrochemical system as set forth in claim 17 further comprising a computer system coupled to the at least one receiver for processing the signal indicative of glucose concentrations.

19. The electrochemical system as set forth in claim 18 wherein the at least one receiver comprises a radio frequency receiver for receiving a serial data signal.

20. The electrochemical system as set forth in claim 18 wherein the computer system comprises a computer network for processing the serial data signal.

21. The electrochemical system as set forth in claim 17 wherein the transmitter comprises a radio frequency transmitter for transmitting a serial data signal.

22. The electrochemical system as set forth in claim 1 wherein the potentiostat circuit comprises:
a first operational amplifier connected to the power supply and the electrochemical sensor for maintaining the first electrode of the electrochemical sensor at a substantially constant excitation voltage;
a second operational amplifier connected to the power supply and the electrochemical sensor for converting the sensor current into an output voltage;
an optocoupler connected to the second operational amplifier for converting the output voltage into a changing resistance value; and a transmitter for transmitting the resistance value to the receiver.

23. The electrochemical system as set forth in claim 22 wherein the power supply comprises:
a first switch having an open and closed position;
a battery connected to the first switch and a first reference voltage; and
a voltage converter connected to a second and third reference voltage.

24. The electrochemical system as set forth in claim 23 wherein the first feedback circuit comprises a direct connection.

25. The electrochemical system as set forth in claim 23 wherein the second operational amplifier comprises:
a third input lead;
a fourth input lead connected to a fourth reference voltage;
a second output lead;
a second switch connected to the third input lead and a second electrode of the electrochemical sensor;
the second switch having an open and closed position;
a third switch connected to the second output lead and the optocoupler;
the third switch having an open and closed position;
a second feedback circuit connected to the second output lead and the third input lead; and
an offset voltage compensation circuit connected to the third input lead and a fifth reference voltage.

26. The electrochemical system as set forth in claim 25 wherein the second feedback circuit comprises a first electrical device in parallel with a second electrical device.

27. The electrochemical system as set forth in claim 26 wherein the first electrical device is a capacitor.

28. The electrochemical system as set forth in claim 26 wherein the second electrical device is a resistor.

29. The electrochemical system as set forth in claim 25 wherein the offset voltage compensation circuit comprises:
a fourth switch connected to the third input lead; and
a variable resistor connected to the fourth switch and the fifth reference voltage.

30. The electrochemical system as set forth in claim 25 wherein the third input lead is an inverting input lead and the fourth input lead is a noninverting input lead.

31. The electrochemical system as set forth in claim 30 wherein the fourth input terminal is at electrical ground.

32. The electrochemical system as set forth in claim 31 wherein the fifth reference voltage is approximately 1.2 volts.

33. The electrochemical system as set forth in claim 22 wherein the first operational amplifier comprises:
a first input lead;
a second input lead;
a first output lead connected to a first electrode of the electrochemical sensor;
a first feedback circuit connected to the first input lead and the first output lead; and
a first potentiometer connected to a first reference voltage, the second input lead and a second reference voltage.

34. The electrochemical system as set forth in claim 33 wherein the first potentiometer comprises a voltage divider connected to a reference voltage, the second input lead and the second reference voltage.

35. The electrochemical system as set forth in claim 33 wherein the first reference voltage is approximately 1.2 volts and the second reference voltage is electrical ground.

36. The electrochemical system as set forth in claim 33 wherein the first input lead is an inverting input lead and the second input lead is a noninverting lead.

37. The electrochemical system as set forth in claim 22 wherein the optocoupler comprises:
a first optical device for generating an optical signal;
a second optical device responsive to the optical signal connected to the transmitter.

38. The electrochemical system as set forth in claim 1 wherein the at least one electrode of the electrochemical sensor comprises a platinum electrode.

39. The electrochemical system as set forth in claim 1 wherein the at least one electrode of the electrochemical sensor is a silver/silver chloride electrode.

40. A telemetry unit for implantation into a body connected to an electrochemical system having at least one electrode therein for detecting analyte concentrations, the telemetry unit comprising:

an electric circuit convertible between a potentiostat circuit and a galvanostat circuit connected to the electrochemical sensor for providing an excitation voltage to a first electrode of the at least one electrode of the electrochemical sensor and generating thereby a first signal indicative of analyte concentrations;

at least one signal converter connected to the convertible electric circuit;

a microprocessor connected to the convertible electric circuit and the at least one signal converter; and a power supply for energizing the electric circuit.

41. The telemetry unit as set forth in claim 40 wherein the electric circuit comprises:

a first operational amplifier having
  a first output terminal connected to a first electrode of the at least one electrode,
  a first switch having at least one position connected to the at least one signal converter,
  a second switch having at least one position connected to the at least one signal converter,
  a first input terminal connected to the first switch, a second input terminal,
  a first feedback circuit having at least one electric device therein connected to a second electrode of the at least one electrode, the second input terminal and the second switch; and a second operational amplifier having
  a third input terminal connected to a third electrode of the at least one electrode,
  a fourth input terminal connected to the at least one signal converter,
  a second output terminal and
  a second feedback circuit having at least one electric device therein connected to the second output terminal, the third input terminal and the microprocessor.

42. The telemetry unit as set forth in claim 41 wherein the first feedback circuit is a negative feedback circuit including a direct connection from the first output terminal to the second input terminal.

43. The telemetry unit as set forth in claim 41 wherein the first feedback circuit is a negative feedback circuit including a first resistor connected to the second input terminal and the second switch.

44. The telemetry unit as set forth in claim 41 wherein the second feedback circuit is a negative feedback circuit including a second resistor connected to the second output terminal and the third input terminal.

45. The telemetry unit as set forth in claim 44 wherein the second resistor is controlled by the microprocessor.

46. The telemetry unit as set forth in claim 41 wherein the second electrode of the at least one electrode is an auxiliary electrode.

47. The telemetry unit as set forth in claim 41 wherein the second electrode of the at least one electrode is a reference electrode.

48. The telemetry unit as set forth in claim 41 wherein the second electrode of the at least one electrode is a working electrode and the third input terminal is disconnected from the third electrode.

49. The telemetry unit as set forth in claim 40 wherein the electric circuit further comprises a filter circuit connected to the potentiostat circuit and the at least one signal converter.

50. The telemetry unit as set forth in claim 40 wherein the electric circuit further comprises a transmitter connected to the microprocessor for transmitting a signal indicative of analyte concentrations.

51. A telemetry unit for implantation into a body connected to an electrochemical system having at least one electrode therein for detecting glucose concentrations, the telemetry unit comprising:

an electric circuit convertible between a potentiostat circuit and a galvanostat circuit connected to the electrochemical sensor for providing an excitation voltage to a first electrode of the at least one electrode of the electrochemical sensor and generating thereby a first signal indicative of analyte concentrations;

at least one signal converter connected to the convertible electric circuit;

a microprocessor connected to the convertible electric circuit and the at least one signal converter; and a power supply for energizing the electric circuit.

52. An electrochemical system for detecting analyte concentrations in a body, the system comprising:

an electrochemical sensor for implantation into the body including at least one electrode;

a telemetry unit for implantation into the body including an electric circuit having a first operational amplifier having a first output terminal connected to a first electrode of the at least one electrode, means for switching the electric circuit between a potentiostat circuit and a galvanostat circuit providing thereby an excitation voltage to a first electrode of the at least one electrode of the electrochemical sensor and generating thereby a first signal indicative of glucose concentrations;

wherein the first operational amplifier includes first and second input terminals connected to means for switching the electric circuit between a potentiostat circuit and a galvanostat circuit and a first feedback circuit having at least one electric device therein connected to a second electrode of the at least one electrode, the second input terminal and means for switching means the electric circuit between a potentiostat circuit and a galvanostat circuit;

at least one signal converter connected to means for switching the electric circuit between a potentiostat circuit and a galvanostat circuit;

a microprocessor connected to means for switching the electric circuit between a potentiostat circuit and a galvanostat circuit and to the at least one signal converter for controlling switching the electric circuit between a potentiostat circuit and a galvanostat circuit;

at least one receiver for receiving the signal from the telemetry unit; and a power supply for energizing the electric circuit.

* * * * *

UNITED STATES PATENT AND TRADEMARK OFFICE
CERTIFICATE OF CORRECTION

PATENT NO. : 6,366,794 B1 Page 1 of 1
APPLICATION NO. : 09/443764
DATED : April 2, 2002
INVENTOR(S) : Francis Moussy et al.

It is certified that error appears in the above-identified patent and that said Letters Patent is hereby corrected as shown below:

Title Page,
Item (73) Assignee, after "(US)" insert --Precision Control Design, Inc., Fort Walton, FL (US)--.
Item (57) Abstract, after "coupled", delete "tlo" and insert therefor --to--.

Column 5,
Line 40, after "first", delete "anaolg" and insert therefor --analog--.
Line 54, after "when the", delete "thirdswitch" and insert therefor --third switch--.
Line 58, after "When the", delete "thirdswitch" and insert therefor --third switch--.

Signed and Sealed this

Twenty-fourth Day of October, 2006

JON W. DUDAS
*Director of the United States Patent and Trademark Office*